United States Patent [19]
Rantanen-Lee et al.

[11] Patent Number: 5,163,913
[45] Date of Patent: Nov. 17, 1992

[54] APPARATUS AND METHOD FOR CONNECTING A CATHETER AND A WINGED INSERTER BODY IN FLUID TIGHT RELATION

[75] Inventors: Ann M. Rantanen-Lee; Roger L. Richins, both of Sandy; Gerald H. Peterson, Salt Lake City; Edmund R. Purdy, Fruitheights, all of Utah

[73] Assignee: Becton, Dickinson and Company, Franklin Lakes, N.J.

[21] Appl. No.: 514,441

[22] Filed: Apr. 25, 1990

[51] Int. Cl.$^5$ ............................................. A61M 5/32
[52] U.S. Cl. ............................................................ 604/177
[58] Field of Search ................. 604/177, 174, 256, 905

[56] References Cited

U.S. PATENT DOCUMENTS

| | | | |
|---|---|---|---|
| 3,802,433 | 4/1974 | Raven | 604/283 |
| 4,177,809 | 12/1979 | Moorehead | 604/165 |
| 4,194,504 | 3/1980 | Harms et al. | 604/177 X |
| 4,300,553 | 11/1981 | Seberg | 604/177 X |
| 4,311,137 | 1/1982 | Gerard | 604/122 X |
| 4,388,074 | 6/1983 | Seberg et al. | 604/177 X |
| 4,389,210 | 6/1983 | Genese | 604/177 |

*Primary Examiner*—John J. Wilson
*Assistant Examiner*—Jeffrey A. Smith
*Attorney, Agent, or Firm*—Arthur D. Dawson

[57] ABSTRACT

An inserter body with a first end and a first part thereon and a second end and a second part thereon includes at passageway aligned along an axis passing through the body. A catheter is held in fluid tight relation with the passageway in the first part by a collar placed to expand the catheter against the passageway. A pair of wings extend in a plane normal to the axis and are joined to the body for folding toward one another without distorting the fluid tight relation of the catheter and the passageway. Areas of stress relief are positioned where the wings and the first part of the body join. A method provides a stress free juncture between the wings of a catheter inserter and the body so that folding the wings during catheter insertion can not distort the junction between the catheter and the passageway through the body. The method includes forming openings between the body and the wings adjacent the part where the catheter is wedged into fluid tight relation with the body passageway.

14 Claims, 2 Drawing Sheets

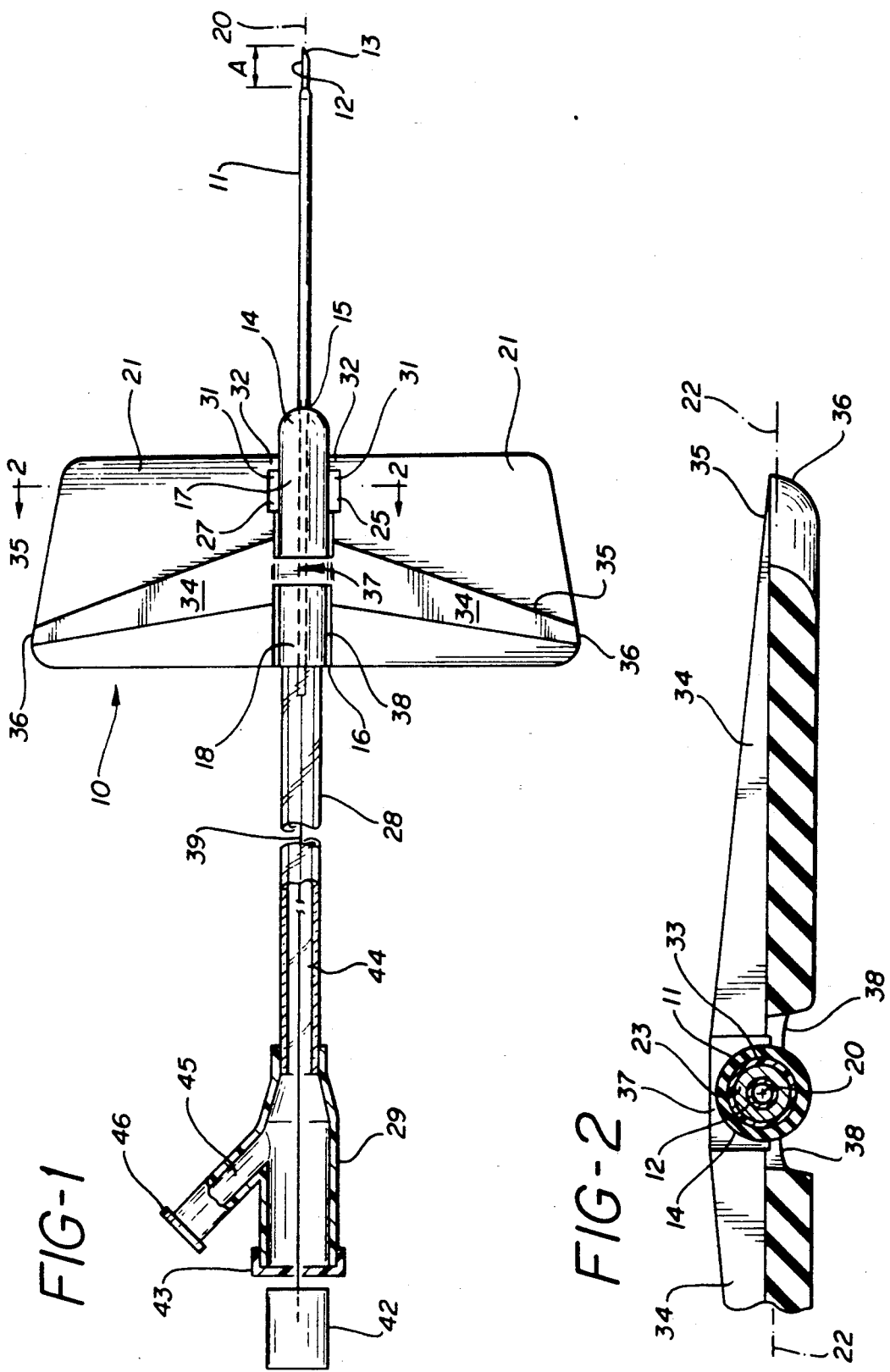

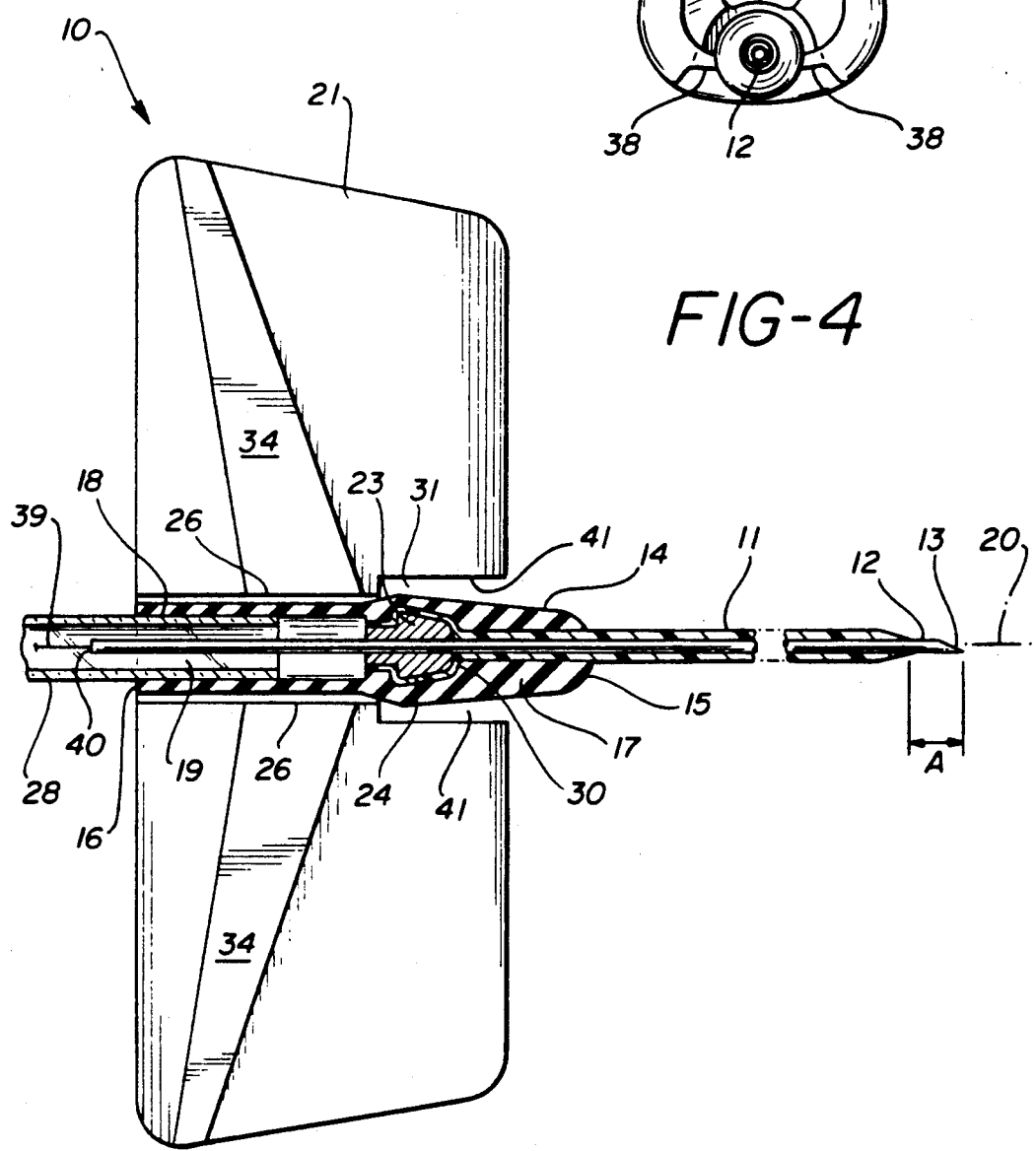

APPARATUS AND METHOD FOR CONNECTING A CATHETER AND A WINGED INSERTER BODY IN FLUID TIGHT RELATION

BACKGROUND OF THE INVENTION

1. Field of the Invention

This invention relates to an apparatus and method for connecting in fluid tight relation a catheter and a winged inserter body, and more specifically, to an apparatus and method for preventing the transmission of stress between the wings and the place here the catheter is wedged against the body passageway when the wings are folded together during us.

2. Background Description

Winged inserters or catheter adapters of the kind wherein the wings are folded toward one another to hold the needle in the catheter during insertion are disclosed in U.S. Pat. Nos. 4,177,809, 4,194,534 and 4,300,553. In these patents a winged adapter facilitates the handling of catheter and a needle during placement into the lumen of a blood vessel. The wings are folded together to distort the body of the adapter and hold the needle axially in the catheter with the needle tip extended from the catheter in position for penetration into the vessel. The interface between the catheter and the winged adapter body has a bond or weld designed and fabricated so as to be flexible because the body is distorted for holding the needle in the catheter. In particular there is an axial relationship between the tip of the needle and the catheter, commonly known as the lie distance, that must be maintained during insertion of the catheter into a vessel when using the tip of the needle to puncture the vessel and thereafter the shank of the needle to carry the catheter into the vessel.

The interface between the catheter and the body has to be fluid tight to prevent leakage of medication or blood which would present a danger to the patient or the practitioner. Catheters, which are not subject to distortion, are connected to their adapters with a fluid tight connection comprising a collar, wedge, insert, eyelet or funnel shaped member fit within the catheter to expand it into the inside wall of the body of the adapter. That arrangement is only used in a wingless over the needle catheter and rigid adapter wherein there is no expectation of distortion. With a wingless catheter a hub carries the needle in coaxial relationship within the catheter whereby engagement between the adapter and the hub maintains the lie distance during catheter insertion. Consequently, the interface between the catheter and the adapter body is not subjected to flexure or distortion which would cause leakage. U.S. Pat. No. 3,802,433 discloses a tubular insert provided so that the catheter tube is expanded into engagement with the inside wall of the adapter.

The expanded connection between the catheter and the adapter offers a secure mechanical connection which eliminates concern about incomplete welds or bonds which might allow the catheter to slip free of the adapter and enter the patient's blood stream. Even though the advantage of the mechanical connection between the catheter and adapter is preferred and recognized as more reliable it has not been successfully used with a winged catheter where the body of the adapter must be distorted to maintain the needle tip lie distance during the penetrating procedure of insertion. The rigidity of the collar, wedge, insert, eyelet or funnel shaped member resists the intended distortion needed to hold and maintain the axial relationship of the needle and catheter. Without the collar, wedge, insert, eyelet or funnel shaped member, stresses applied, to pinch the needle when the wings are folded, would also distort the interface between the catheter and the adapter. A solution to the problems of reliably holding the catheter with fluid tight juncture while permitting distortion of the winged adapter body to maintain the axial relationship of the needle and catheter has not been found.

SUMMARY OF THE INVENTION

A catheter inserter comprises an adapter or body with a first end and a second end and a first part on the first end and a second part on the second end. The body has a passageway aligned along an axis of the body and passing therethrouqh and a pair of wings extending outwardly from the body. A catheter mounted in the first part of the body extends from the first end in alignment with the axis of the passageway and in fluid tight communication therewith. A funnel shaped hollow member fits within the catheter coaxial with the axis to expand the catheter against the passageway for maintaining the catheter within the body passageway end within the first part. A larger part of the funnel shaped member is located facing toward the second part. An area of maximum stress relief is positioned in a junction between each of the pair of wings and the body near the first part wherein the funnel shaped hollow member fits within the catheter.

A preferred form of the inserter may include an opening disposed in each wing on opposite sides of the body as the area of maximum stress relief between the body and each wing. Thus the first part of the body extends along the axis independent of the pair of wings as a nose for supporting the catheter in fluid tight relation while remaining free from a transmitting stresses generated in the wings during bending when handling and holding.

Each opening may preferably be of a shape that forms an elongate section with the longer dimension parallel to the axis of the body and of a length approximately the same as the first part. Each elongate section may have web of material spanning transversely at least a part thereof between the wing and the body wherein the web material is incapable of transmitting stress between the wing and the body such that the fluid tight relation between the catheter and the body remains uneffected during the handling and holding of the wings. The web material is preferably positioned near the first end of the body nose across the elongate section and normal to the axis of the body. The elongate section may have a generally rectangular shape.

In the preferred embodiment a cross bar stretches between each wing across the body between a raised portion on one wing to another raised portion of the other wing. The cross bar is integral and in transverse relation to the body about midway between the first and second ends. Each raised portion tapers from the cross bar into the surface of the wing at the outer side of each wing away from the body. Upon the folding of the wings toward one another along a direction normal to the axis of the body, the raised portions and the cross bar pinch the body causing the passageway therein to tighten about the needle. The body is preferably molded of a flexible polymeric substance.

An extension tube may be provided in fluid communication with the passageway and mounted in the second part to extend outwardly from the second end with a fitting on the tube located away from the second end. The inserter of may also carry a needle with a hollow tubular shank ending with a beveled tip used for insertion of the catheter. The needle is carried for axial sliding relation within the catheter so the tip of the needle extends beyond the catheter for penetrating the skin when inserting the catheter and needle into a vessel or artery lumen.

The inserter and needle assembly preferably includes a flexible wire connected to the needle end away from the tip. The wire extends from the needle permitting handling of the needle remotely of the tip enabling the needle to be axially pulled through the catheter and the passageway for removal of the needle after insertion of the catheter with an over the needle procedure. Each wing includes a hinge positioned in a juncture alongside the body where each wing joins the body. Each hinge preferably extends parallel to the axis of the body and coextensive with the length thereof between the elongate section opening and the second end of the body but interrupted at the cross bar.

A method for providing a stress relief between the wings of an inserter and the internally reinforced catheter supporting end of the inserter includes providing a catheter inserter having a body with a first end and a second end and a first part on the first end and a second part on the second end. The method requires locating a passageway through the first part from the first end and through the body to the second end and positioning a catheter in fluid tight relation with the passageway in the first part of the body and extending from the first end. The method further includes holding the catheter in fluid tight relation to the passageway with wedging eyelet or funnel shaped member inserted within the catheter to expand the end thereof against an inside wall of the passageway. The preferred method may have a pair of wings extending laterally from the body wherein the wings are located in a plane being attached to opposite sides of the body second part. The method may also require providing a hinged juncture between each wing and the body.

BRIEF DESCRIPTION OF THE DRAWINGS

FIG. 1 is a top plan view of the preferred embodiment of a winged catheter inserter with an extension tube and Y fitting shown in section.

FIG. 2 is a sectional view of the winged inserter taken along line 2—2 of FIG. 1.

FIG. 3 is an illustration of an end view as would be seen when looking toward the needle end of the winged inserter such as in FIG. 1 wherein the wings are in a folded or catheter insertion position.

FIG. 4 is a top plan view of an alternate embodiment of winged inserter which is similar to that shown in FIG. 1 except the openings about the junctures of the wings and the adapter body are of slightly different configuration, and the catheter and extension tube are shown in cross section.

DETAILED DESCRIPTION

While this invention is satisfied by embodiments in many different forms, there is shown in the drawings and will herein be described in detail a preferred embodiment and an alternate embodiment of the invention, with the understanding that the present disclosure is to be considered as exemplary of the principles of the invention and is not intended to limit the invention to the embodiments illustrated. The scope of the invention will be measured by the appended claims and their equivalents.

FIG. 1 is a top plan view illustrating the overall appearance of the preferred embodiment of the winged catheter inserter 10 used for carrying a tube or catheter 11 and its needle 12 into the lumen of a blood vessel. A needle tip 13 penetrates the blood vessel and carries the leading edge of the catheter 11 with it into the lumen of the blood vessel during an insertion with an over the needle procedure.

The preferred catheter inserter 10 comprises an adapter or body 14 with a first end 15 and a second end 16 and a first part 17 on the first end 15 and a second part 18 on the second end 16 as seen in FIG. 4. The body 14 has a passageway 19 aligned along an axis 20 of the body 14 and the passageway 19 passes therethrough allowing fluid flow through the body 14. A pair of wings 21 extend outwardly from the body 14 and define the plane 22 for use in securing the inserted catheter to the patient as shown in FIG. 2. The wings 21 are also used in handling and holding the inserter 10 during placement with an over the needle technique familiar to medical practitioners.

The catheter 11 in the form of a small diameter flexible plastic tube is mounted in the first part 17 of the body 14 and extending from the first end 15 in alignment with the axis 20 of the passageway 19 and in fluid communication therewith. To secure the catheter 11 a relatively rigid eyelet, insert, collar or funnel shaped hollow member 23 is in the preferred assembly fit within the catheter 11 tube and coaxial with the axis 20 to expand the catheter 11 against the passageway 19 as in FIGS. 2 and 4. Thus the funnel shaped hollow member 23 is designed for maintaining the catheter 11 within the first part 17 of the passageway 19 of the body 14. A larger part 24 of the funnel shaped hollow member 23 is located facing toward the second part 18 to function as a transition for flow passing from the second part 18 to the first part 17 of the passageway.

An area of maximum stress relief 25 is required in the preferred inserter 10 positioned at a junction 26 between each of the pair of wings 21 and the body 14 near the first part 17 adjacent to the locale where the funnel shaped hollow member 23 fits within the catheter 11, but outside the body 14. A recess or opening 27 is disposed in each wing 21 on opposite sides of the body 14 to provide maximum stress relief in the area of maximum stress relief 25. That is to say that between the body 14 and each wing 21 as part of the area of maximum stress relief 25 there are openings 27 that provide the stress relief. The first part 17 of the body 14 extends along the axis 20 independent of the pair of wings 21 as a nose of the body 14 for supporting the catheter 11 in fluid tight relation while remaining free from transmitting stresses from the wings 21 during bending when inserting.

An extension tube 28 in fluid communication with the passageway 19 and mounted in that second part 18 of the body 14 extends outwardly from the second end 16 and aligned coaxial to the axis 20. The extension tube 28 includes a fitting 29 away from the second end 16. As seen in FIG. 1 the fitting 29 is Y shaped having a channel in alignment with the axis 20 and another channel with a passage intersecting the axis 20 at an angle. The Y fitting 29 permits two means for access to the passageway 19 in the body 14; in particular, for insertion and use.

The needle 12 fashioned of a thin wall metal cannula with a hollow tubular portion or shank 30 and a beveled tip 13 fits in sliding relation within the catheter 11. The tip 13 is located away from the body 14 so the tip 13 of the needle 12 extends beyond the catheter 11 and is set for penetration when inserting the catheter 11 and needle 12 into a lumen of a blood vessel. The needle 12 is movable axially through the catheter 11, the body 14, passageway 19 and the extension tube 28 during removal of the needle 12 after insertion of the catheter 11 with an over the needle procedure.

Each opening 27 in the preferred form of the inserter 10 is shaped to form an elongate section 31 with its longer dimension substantially parallel to the axis 20 of the body 14 and is of a length approximately the same as the funnel shaped hollow member 23. Each elongate section 31 has a web 32 of material spanning transversely at least part thereof and each web 32 spans the gap between the wing 21 and the body 14. The web 32 is of a soft polymeric material with a thickness such that it does not transmit sufficient stress from wing 21 to distort body 14. Consequently, the fluid tight relation at an interface 33 between the catheter 11 and the body 14 nose or first part 17 remains uneffected because it is unstressed during the handling and holding of the wings 21. The material of web 32 is positioned near the first end of the body 14 across the elongate section 31 and normal to the axis 20 of the body 14. The elongate section 31 has a generally rectangular configuration as best seen in FIG. 1.

As shown in the FIGS. 1 through 4 each wing 21 includes a raised portion 34 which tapers from the body 14 into a top surface 35 of the wing 21 at an outer side 36 of each wing 21. A cross bar 37 is located about midway between the first and second ends 15 and 16 and is stretched across the body 14 between one raised portion 34 of one wing 21 to the other raised portion 34 of the other wing 21 in transverse relation to and in contact with the body 14. Upon folding the wings 21 toward one another along a direction normal to the axis 20 of the body 14, the raised portions 34 and the cross bar 37 pinch and distort the body 14 causing the passageway 19 therein to constrict about the needle 12. A hinge 38 is positioned along side the body 14 at a juncture where each wing 21 joins the body 14. Each hinge 38 extends between the opening 27 and the second end 16 of the body 14, each hinge 38 being substantially parallel to the axis 20 of the body 14 and coextensive with the length thereof except where interrupted by the cross bar. The preferred body 14 is injection molded of flexible polymeric substance such as polyurethane, polyvinyl chloride or the like.

A flexible wire 39 is connected to the needle 12 at an end 40 away from the tip 1. The wire 39 extends from the needle 12 through the extension tube 28 permitting handling of the needle 12 remotely of the tip 13, see FIGS. 1 and 4. The wire 39 enables the needle 12 to be axially pulled through the catheter 11, the passageway 19 and the extension tube 28 for removal of the needle 12 after insertion of the catheter 11 with an over the needle procedure.

In an alternate form of the invention shown in FIG. 4, recess 41 is part of each wing 21 adjacent the first part 17. Each recess 41 extends from the first end 15 into each wing 21. Each recess 41 has a dimension parallel to the axis 20 of the body 14 greater than its dimension normal to the axis 20. The primary difference between the preferred inserter embodiment of FIG. 1 and the alternate inserter embodiment of FIG. 4 is that the former has web 32 and the later does not have web 32.

A preferred method for providing a stress relief 25 between the wings 21 of the body 14 and the internally reinforced catheter 11 includes several steps. In particular, providing the body 14 with the first end 15 and the second end 16 and the first part 17 on the first end 15 and the second part 18 on the second end 16 is a step of the preferred method. Moreover, locating passageway 19 through the first part 17 from the first end 15 and through the body 14 to the second end 16 is another step of the method of the present invention.

Also positioning the catheter 11 in fluid tight relation with the passageway 19 in the first part 17 of the body 14 and extending from the first end 15 forms another step in the method. While holding the catheter 11 in fluid tight relation to the passageway 19 with the funnel shaped member 23 inserted within the catheter 11 to expand the end thereof against the passageway 19 is the step of the method that provides a safer catheter inserter 10. To facilitate handling during insertion of the catheter 11 the step of extending laterally the wings 21 located on opposite sides of the body 14 and in the plane 22. The final step is providing the junction 26 between each wing 21 and the body 14.

Another and further step of the preferred method includes locating cross bar 37 transverse to the body 14 and overlying the wings 21 and tapering the cross bar 37 from the raised portions 34 at the body 14 to the surface 35 of each wing 21 at the part 36 of each wing which is away from the body 14. The method may also have the added step of providing extension tube 28 in fluid communication with the passageway 19 in second end 16. The method can have the additional step of placing fitting 29 on an end of the extension tube 28 which is remote of the second end 16.

In use the wings 21 of inserter 10 are pinched together as shown in FIG. 3. This distorts the body 14 about the shank 30 of the needle 12 retaining the needle 12 within the catheter 11 with the appropriate lie distance A such as shown in FIGS. 1 and 4. The inserter 10 may be used to place the needle 12 and the catheter 11 into the lumen of a blood vessel. By inserting the tip 13 through the skin and into the lumen carrying the catheter 11 with the needle via support on the shank 30 of the needle 12. Once the needle 12 is inserted with the catheter 11 into the lumen, the wings 21 are released and folded flat into their plane 22 so the needle catheter 11 may be advanced over the tip of the needle 12 into the lumen of the blood vessel.

The wire 39 which terminates with a knob 42 which can be pulled to the left in FIG. 1 for removing the needle from the catheter 11, the passageway 19 and the extension tube 28. A flexible seal 43 may be provided across a channel 44 which is in line with the axis 20 of the inserter 10. Channel 44 is in part of fitting 29.

Another channel 45 forms the Y of fitting 29 and intersects with channel 44 to provide a luer attachment 46 for infusing or taking fluid from the extension tube 28 when the catheter 11 is placed within the lumen of a blood vessel. FIG. 3 shows the distortion of the cross bar 37 and the body 14 about the catheter 11 and the needle 12. Raised portions 34 cooperate and bear against the body 14 and pinch the needle 12 by constricting the passageway 19. Because seal 43 is a resilient material and the wire 39 is of very fine diameter, it is wiped by the seal 43 as knob 42 is pulled away from fitting 29. This provides an essentially bloodless technique in placing the inserter 10.

Those skilled in the art will appreciate that the area of stress relief 25 may take many forms and still be capable of permitting the nose portion of the winged adapter to provide a fluid tight connection. In particular, when the wings 21 are folded together the reinforced connection between the catheter 11 and the body 14, should not be subject to stress which would cause material deformation resulting in a leak. The specific material described and the particular configurations of the preferred and alternate embodiments may be changed without departing from the scope of the invention covered by the claims which follow.

What is claimed is:

1. A catheter inserter comprising:
    a body with a first end and a second end and a first part on the first end and a second part on the second end, the body having a passageway aligned along an axis of the body and passing therethrough, the body having a pair of wings extending outwardly from the body for use in handling and holding, said body being formed from a flexible polymeric substance;
    a tube mounted in the first part of the body and extending from the first end in alignment with the axis of the passageway and in fluid communication therewith;
    a funnel-shaped hollow member fit within the tube coaxial with the axis to expand the tube against the passageway for maintaining the tube within the body passageway and within the first part with a larger part of the funnel shaped member being located facing toward the second part; and
    an area of maximum stress relief positioned in a junction between each wing of the pair and the body near the first part where the funnel-shaped hollow member fits within the tube.

2. The inserter of claim 1 wherein an opening is disposed in each wing on opposite sides of the body to provide the areas of maximum stress relief between the body and each wing so the first part extends along the axis independent of the pair of wings as nose of the body for supporting the tube in fluid tight relation while remaining free from transmitted stresses during bending when handling and holding the wings.

3. The inserter of claim 2 wherein each opening is of a shape that forms an elongate section with its longer dimension substantially parallel to the axis of the body and of a length approximately the same as the funnel shaped hollow member.

4. The inserter of claim 3 wherein each elongate section has a thin web of material spanning transversely at least a part thereof and between the wing and the body but the web material being incapable of transmitting stress between the wing and the body such that the fluid tight relation between the tube and the body remains unaffected during the handling and holding of the wings.

5. The inserter of claim 4 wherein the web material is positioned near the first end of the body nose across the elongate section and normal to the axis of the body.

6. The inserter of claim 5 wherein the elongate section has a generally rectangular configuration.

7. The inserter of claim 2 wherein each wing includes a hinge positioned alongside the body where each wing joins the body, each hinge being substantially parallel to the axis of the body and coextensive with the length thereof between the opening and the second end of the body.

8. The inserter of claim 1 wherein the body includes an extension tube in fluid communication with the passageway and mounted in the second part and extending outwardly from the second end coaxially to the axis.

9. The inserter of claim 8 wherein the extension tube includes a fitting away from the second end.

10. The inserter of claim 9 wherein a hollow tubular shank needle having a beveled tip fits in sliding relation within the tube away from the body with the tip of the needle extending beyond the tube for penetration into a lumen of a vessel when inserting the tube and needle, and wherein the needle is movable axially through the tube, the passageway and the extension tube for removal of the needle from the tube after insertion with an over the needle procedure.

11. The inserter of claim 10 wherein each wing includes a raised portion which tapers from the body into a top surface of the wing at an outer side of each wing, and a cross bar located about midway between the first and second ends stretches across the body between one raised portion of one wing to the other raised portion of the other wing in transverse relation to and in contact with the body, so that upon the folding of the wings toward one another along a direction normal to the axis of the body, the raised portions and the cross bar pinch the body causing the passageway therein to constrict about the needle.

12. The inserter of claim 10 wherein a flexible wire is connected to the needle away from the tip and extends from the needle through the extension tube permitting handling of the needle remotely of the tip enabling the needle to be axially pulled through the tube, the passageway and the extension tube for removal of the needle from the tube after insertion with an over the needle procedure.

13. A catheter inserter and adapter comprising:
    a winged body with a first end and a second end and a first part on the first end and a second part on the second end, the body having a passageway aligned along an axis of the body and passing through the first part from the first end into the body, the body having a pair of laterally extending wings each extending in a plane normal to the body;
    a cross bar located transversely across the body and across each wing as an integral part thereof, the cross bar providing an area of resistance to bending between the wings and the body during folding of the wings toward one another along a direction normal to the axis of the body; and
    a recess as part of each wing adjacent the first part extending from the first end into each wing, each recess having a dimension substantially parallel to the axis of the body which is greater than its dimension normal to the axis.

14. A method for providing a stress relief between the wings of an inserter and an internally reinforced catheter connected to inserter body including the following steps:
    providing a catheter inserter having a body with a first end and a second end and a first part on the first end and a second part on the second end;
    locating a passageway through the first part from the first end and through the second part to the second end;

positioning a catheter in fluid tight relation with the passageway in the first part of the body and extending from the first end;

holding the catheter in fluid tight relation to the passageway with a hollow wedging eyelet inserted axially into the catheter to expand the end thereof against an inside wall of the passageway;

extending laterally from the body a pair of wings having a cross bar transverse to the body and overlying the wings, said wings located on opposite sides of the body second part in a plane;

providing a hinged juncture between each wing and the body; and tapering the cross bar from raised portions near the body to the surface of each wing at the part of each which is away from that body.

* * * * *